US007531309B2

(12) United States Patent
Davies et al.

(10) Patent No.: US 7,531,309 B2
(45) Date of Patent: May 12, 2009

(54) PCR BASED CAPSULAR TYPING METHOD

(75) Inventors: Dele Davies, Okemos, MI (US); David W. Lacher, Lansing, MI (US); Thomas S. Whittam, Okemos, MI (US); Shannon Manning, Howell, MI (US)

(73) Assignee: Michigan State University, Lansing, MI (US)

(*) Notice: Subject to any disclaimer, the term of this patent is extended or adjusted under 35 U.S.C. 154(b) by 0 days.

(21) Appl. No.: 11/294,830

(22) Filed: Dec. 6, 2005

(65) Prior Publication Data

US 2007/0128613 A1 Jun. 7, 2007

(51) Int. Cl.
*C12Q 1/68* (2006.01)
(52) U.S. Cl. .......................... 435/6; 435/91.1; 435/91.2
(58) Field of Classification Search ........................ None
See application file for complete search history.

(56) References Cited

U.S. PATENT DOCUMENTS

| 2003/0215802 | A1 | 11/2003 | Jannes et al. | |
|---|---|---|---|---|
| 2003/0228599 | A1 | 12/2003 | Struas | |
| 2004/0023209 | A1 | 2/2004 | Jonasson | |
| 2004/0219517 | A1 | 11/2004 | Ecker et al. | |
| 2004/0253517 | A1 | 12/2004 | Young-Jun et al. | |
| 2004/0253617 | A1 | 12/2004 | Young-Jun et al. | |
| 2006/0160121 | A1* | 7/2006 | Mounts et al. ................. | 435/6 |

FOREIGN PATENT DOCUMENTS

| WO | WO 99/51771 | 10/1999 |
|---|---|---|
| WO | WO 03/080870 | 10/2003 |

OTHER PUBLICATIONS

Cieslewicz et al., "Structural and Genetic Diversity of Group B Streptococcus Capsular Polysaccharides," Infection and Immunology, May 2005, vol. 73, No. 5, pp. 3096-3103.*
Lu et al., "Use of PCR with Universal Primers and Restriction Endonuclease Digestions for Detection and Identification of Common Bacterial Pathogens in Cerebrospinal Fluid," J. Clinical Micro., Jun. 2000, vol. 38, No. 6, pp. 2076-2080.*
Sellin et al., "Genotyping of the Capsule Gene Cluster (cps) in Nontypeable Group B Streptococcus Reveals Two Major cps Allelic Variants of Serotypes III and VII," J.Clinical Micro., Sep. 2000, vol. 38, No. 9, pp. 3420-3428.*
Buck et al., "Design Strategies and Performance of Custom DNA Sequencing Primers," Biotechniques, Sep. 1999, vol. 27, No. 3, pp. 528-536.*
Lawrence et al., Evaluation of Serotype Prediction by cpsA-cpsB Gene Polymorphism in *Streptococcus pneumoniae*; J. Clin. Microbiol 38:1319 (2000).
Lawrence et al.,Evaluation of Semiautomated Multiplex PCR Assay for Determination of *Streptococcus pneumoniae* Serotypes and Serogroups; J. Clin Microbiol 41:601 (2003).
Tettelin et al., Complete genome sequence and comparative genomic analysis of an emerging human pathogen, serotype V *Streptococcus agalactiae*; PNAS 99:12391 (2002).

Chaffin et al., The Serotype of Type Ia and III Group B Streptococci Is Determined by the Polymerase Gene within the Polycistronic Capsule Operon; J. Bacteriol. 182:4466 (2000).
Harrison et al., Serotype distribution of invasive group B streptococci isolates in Maryland: implications for vaccine formulation. Maryland Emerging Infections Program.; 1998 J. Infect. Disease 177:998.
Hickman et al., Changing Epidemiology of Group B Streptococcal Colonization; 1999 Pediatrics 104:203.
Wilkinson and Moody, Serological Relationships of Type I Antigens of Group B Streptococci; 1969 J. Bacteriol. 97:629.
Holm and Hakansson, A simple and sensitive enzyme immunoassay for determination of soluble type-specific polysaccharide from group B streptococci.; 1988 J. Immunol. Methods 106:89.
Hakansson et al., Novel coagglutination method for serotyping group B streptococci.; 1992 J. Clin. Microbiol. 30:3268.
Triscott and Davies, A comparison of four methods for the serotyping of group B streptococci.; 1979 Aust. J. Expt. Biol. Med. Sci. 57:521.
Zuerlein et al., Latex agglutination detection of group-B streptococcal inoculum in urine.; Diagn Microbiol Infect Dis, May 1991; 14(3): 191-4.
Cropp et al., Serotyping of group B streptococci by slide agglutination fluorescence microscopy, and microimmunodiffusion.; J Lab Clin Med, Oct. 1974; 84(4): 594-603.
Arakere et al., Inhibition Enzyme-Linked Immunosorbent Assay for Serotyping of Group B Streptococcal Isolates; 1999 J. Clin. Microbiol. 37:2564.
Rolland et al., Genetic Features of *Streptococcus agalactiae* Strains Causing Severe Neonatal Infections, as Revealed by Pulsed-Field Gel Electrophoresis and hylB Gene Analysis; 1999 J. Clin. Microbiol. 37:1892.
Nagano et al.,Restriction endonuclease digest patterns of chromosomal DNA from group B beta-haemolytic streptococci; 1991 J. Medical Microbiol. 35:297.
Baker and Edwards, Group B streptococcal conjugate vaccines; 2003. Arch. Dis. Child. 88:375-378.
Blumberg et al., Invasive group B streptococcal disease: the emergence of serotype V.; 1996. J. Infect. Dis. 173:365-373.
Farley et al., Group B Streptococcal disease in nonpregnant adults.; 2001. Clin. Infect. Dis. 33:556-561.
Zaleznik et al., Invasive disease due to group B Streptococcus in pregnant women and neonates from diverse population groups.; 2000. Clin. Infect. Dis. 30:276-281.
Lancefield, A Serological Differentiation of Specific Types of Bovine Hemolytic Streptococci (Group B); 1934. J. Exp. Med. 59:441-458.
Park et al., Detection of Group B Streptococcal Colonization in Pregnant Women Using Direct Latex Agglutination Testing of Selective Broth; 2001. J. Clin. Microbiol. 39:408-409.
Slotved et al., Latex Assay for Serotyping of Group B Streptococcus Isolates; 2003. J. Clin. Microbiol. 41:4445-4447.
Johnson and Ferrieri, Group B streptococcal Ibc protein antigen: distribution of two determinants in wild-type strains of common serotypes.; 1984. J. Clin. Microbiol. 19:506-510.

(Continued)

*Primary Examiner*—Gary Benzion
*Assistant Examiner*—Heather G Calamita
(74) *Attorney, Agent, or Firm*—Medlen & Carroll, LLP (57) ABSTRACT

The present invention relates to molecular diagnostics. In particular, the present invention relates to PCR based diagnostics for the typing of Group B streptococci.

3 Claims, 3 Drawing Sheets

OTHER PUBLICATIONS

Bliss et al., Group B Streptococcus colonization in male and non-pregnant female university students: a cross-sectional prevalence study.; 2002. Clin. Infect. Dis. 34:184-190.

Edwards et al., Group B streptococcal colonization and serotype-specific immunity in healthy elderly persons.; 2005. Clin. Infect. Dis. 40:352-357.

Kong et al., Serotype Identification of Group B Streptococci by PCR and Sequencing; 2002. J. Clin. Microbiol. 40:216-226.

Davies et al., Population-based active surveillance for neonatal group B streptococcal infections in Alberta, Canada: implications for vaccine formulation.; 2001. Pediatr. Infect. Dis. J. 20:879-884.

Davies et al., Antibodies to capsular polysaccharides of group B Streptococcus in pregnant Canadian women: relationship to colonization status and infection in the neonate.; 2001. J. Infect. Dis. 184:285-291.

Manning et al., Determinants of co-colonization with group B streptococcus among heterosexual college couples.; 2002. Epidemiology 13:533-539.

Borchardt et al., Comparison of DNA Dot Blot Hybridization and Lancefield Capillary Precipitin Methods for Group B Streptococcal Capsular Typing; 2004. J. Clin. Microbiol. 42:146-150.

* cited by examiner

SEQUENCE LISTING

```
<160> NUMBER OF SEQ ID NOS: 3

<210> SEQ ID NO 1
<211> LENGTH: 24
<212> TYPE: DNA
<213> ORGANISM: Streptococcus agalactiae

<400> SEQUENCE: 1
gtgttcattc aaacgggtta ctca                                          24

<210> SEQ ID NO 2
<211> LENGTH: 23
<212> TYPE: DNA
<213> ORGANISM: Streptococcus agalactiae

<400> SEQUENCE: 2
gaacttaaag aaccgctcgt ctg                                           23
```

```
<210> SEQ ID NO 3
<211> LENGTH: 19
<212> TYPE: DNA
<213> ORGANISM: Streptococcus agalactiae

<400> SEQUENCE: 3
ccggcaagat atggtggat                                                19
```

PCR BASED CAPSULAR TYPING METHOD

This Application was supported in part by NIH grant 1R01AI1066081-01. The government may have certain rights in the invention.

FIELD OF THE INVENTION

The present invention relates to molecular diagnostics. In particular, the present invention relates to PCR based diagnostics for the typing of Group B streptococci.

BACKGROUND OF THE INVENTION

Group B streptococci (GBS; *Streptococcus agalactiae*), although generally carried asymptomatically, can cause invasive disease in newborns, pregnant women, and immunocompromised adults. Group B *streptococcus* is the most common cause of neonatal and obstetric sepsis and an increasingly important cause of septicaemia in the elderly and immunocompromised patients. The incidence of neonatal GBS sepsis has been reduced in recent years by the use of intrapartum antibiotic prophylaxis, but there are many problems with this approach.

Knowledge of the distribution of GBS types (including capsular polysaccharide gene serotypes, serosubtypes; protein antigen gene subtypes; and mobile genetic element subtypes) is needed to determine the optimal formulation of vaccine antigens and in diagnostic and research applications. Type distribution based on one geographic location or small numbers of patients may not be generally applicable. Continued monitoring will be necessary to assess the prevalence of different GBS types.

Nine capsular polysaccharide GBS serotypes have been described (Harrison et al., 1998J. Infect. Disease 177:998; Hickman et al., 1999 Pediatrics 104:203). Various serotyping methods have been used, including immuno-precipitation (Wilkinson and Moody, 1969 J. Bacteriol. 97:629), enzyme immunoassay (Holm and Hakansson, 1988 J. Immunol. Methods 106:89), coagglutination (Hakansson et al., 1992 J. Clin. Microbiol. 30:3268), counter-immunoelectrophoresis, and capillary precipitation (Triscott and Davies, 1979 Aust. J. Expt. Biol. Med. Sci. 57:521), latex agglutination (Zuerlein et al., 1991), fluorescence microscopy (Cropp et al., 1974) and inhibition-ELISA (Arakere et al., 1999 J. Clin. Microbiol. 37:2564). These methods are labour-intensive and require high-titered serotype-specific antisera, which are expensive and difficult to make and commercially available for only six serotypes—Ia to V (Arakere et al., 1999, supra). Molecular genotyping methods, such as pulsed-field gel electrophoresis (Rolland et al., 1999J. Clin. Microbiol. 37:1892), restriction endonuclease analysis (Nagano et al., 1991 J. Medical Microbiol. 35:297) are useful for epidemiological studies but do not generally identify serotypes. Consequently, there is a need for a reliable molecular method for GBS serotype identification.

SUMMARY OF THE INVENTION

The present invention relates to molecular diagnostics. In particular, the present invention relates to PCR based diagnostics for the typing of Group B streptococci.

Accordingly, in some embodiments, the present invention provides a method, comprising: providing a sample comprising group B *streptococcus*; contacting the sample with at least two primers under conditions such that an amplicon comprising at least a portion of at least one capsular gene of said group B *streptococcus* is produced; and contacting the amplicon with at least one restriction enzyme under conditions such that a plurality of restriction fragments are generated. In some embodiments, the method further comprises the step of determining the serotype of the group B *streptococcus* based on the size of the plurality of restriction fragments. In some embodiments, the serotype is Ia, Ib, II, III, IV, V, VI, VII, or VIII. In some embodiments, the amplicon comprises a variable region of the group B *streptococcus* capsular genome. In some embodiments, the first primer (e.g., SEQ ID NO:1) hybridizes to the cpsG gene and the second primer (e.g., SEQ ID NO:2) hybridizes to the cpsL gene. In other embodiments, the first primer (e.g., SEQ ID NO:3) hybridizes to the cpsR gene and the second primer (e.g., SEQ ID NO:2) hybridizes to the cpsL gene. In some embodiments, the restriction enzyme is DdeI.

The present invention further comprises a kit, comprising at least two primers configured to amplify at least a portion of at least one capsular gene of a group B *streptococcus*; and a restriction enzyme configured to recognize at least one restriction site in the at least one capsular gene of the group B *streptococcus*. In some embodiments, the at least one capsular gene comprises a variable region of the group B *streptococcus* capsular genome. In some embodiments, the first primer (e.g., SEQ ID NO:1) hybridizes to the cpsG gene and the second primer (e.g., SEQ ID NO:2) hybridizes to the cpsL gene. In other embodiments, the first primer (e.g., SEQ ID NO:3) hybridizes to the cpsR gene and the second primer (e.g., SEQ ID NO:2) hybridizes to the cpsL gene. In some embodiments, the restriction enzyme is DdeI.

DEFINITIONS

To facilitate an understanding of the present invention, a number of terms and phrases are defined below:

As used herein, the term "single nucleotide polymorphism" or "SNP", refers to any position along a nucleotide sequence that has one or more variant nucleotides. Single nucleotide polymorphisms (SNPs) are the most common form of DNA sequence variation found in the human genome and are generally defined as a difference from the baseline reference DNA sequence which has been produced as part of the Human Genome Project or as a difference found between a subset of individuals drawn from the population at large. SNPs occur at an average rate of approximately 1 SNP/1000 base pairs when comparing any two randomly chosen human chromosomes. Extremely rare SNPs can be identified which may be restricted to a specific individual or family, or conversely can be found to be extremely common in the general population (present in many unrelated individuals). SNPs can arise due to errors in DNA replication (i.e., spontaneously) or due to mutagenic agents (i.e., from a specific DNA damaging material) and can be transmitted during reproduction of the organism to subsequent generations of individuals.

As used herein, the term "subject" refers to any animal (e.g., a mammal), including, but not limited to, humans, non-human primates, rodents, and the like. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxymethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 5 kb or more on either end such that the gene corresponds to the length of the full-length mRNA. Sequences located 5' of the coding region and present on the mRNA are referred to as 5' untranslated sequences. Sequences located 3' or downstream of the coding region and present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decreases production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH₂PO₄.H₂O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH₂PO₄.H₂O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "detection assay" refers to an assay for detecting the presence of absence of variant nucleic acid sequences (e.g., subtypes, polymorphism or mutations) in a given allele or nucleic acid (e.g., Group B strep).

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like, as well as pathogens (e.g., viruses) isolated from such samples. Environmental samples include environmental material such as surface matter, soil, water and industrial samples. Such examples are not however to be construed as limiting the sample types applicable to the present invention.

DETAILED DESCRIPTION OF THE INVENTION

The present invention relates to molecular diagnostics. In particular, the present invention relates to PCR based diagnostics for the typing of Group B streptococci.

A crucial factor in GBS virulence is the production of an antigenically variable polysaccharide capsule, also used for strain typing. Certain serotypes of the nine known types (Ia, Ib, and II to VIII) are more prevalent in invasive disease, e.g., serotypes Ia, II, and III, and, since the early 1990s, serotype V (Baker and Edwards, 2003. Arch. Dis. Child. 88:375-378; Blumberg et al., 1996. J. Infect. Dis. 173:365-373; Farley et al., 2001. Clin. Infect. Dis. 33:556-561; Harrison et al., 1998. J. Infect. Dis. 177:998-1002; Zaleznik et al., 2000. Clin. Infect. Dis. 30:276-281).

Because of the role of the capsule in GBS virulence, several phenotypic methods have been devised for serotyping, including the Lancefield capillary precipitin method (Lancefield, 1934. J. Exp. Med. 59:441-458), the predominant serotyping scheme, latex agglutination (Park et al., 2001. J. Clin. Microbiol. 39:408-409; Slotved et al., 2003. J. Clin. Microbiol. 41:4445-4447), coagglutination (Hakansson et al., 1992. J. Clin. Microbiol. 30:3268-3269), double immunodiffusion (Johnson and Ferrieri, 1984. J. Clin. Microbiol. 19:506-510), and enzyme immunoassays (Arakere et al., 1999. J. Clin. Microbiol. 37:2564-2565). These, however, generally have limited accuracy and applicability, are expensive, and result in numerous (approximately 2 to 18%) non-typeable (NT) isolates (Bliss et al., 2002. Clin. Infect. Dis. 34:184-190; Blumberg et al., 1996. J. Infect. Dis. 173:365-373; Edwards et al., 2005. Clin. Infect. Dis. 40:352-357). Genotypic methods, including PCR and sequencing of serotype-specific gene fragments within the cps genes (Cieslewicz et al., 2005. Infect. Immun. 73:3096-3103; Kong et al., 2002. J. Clin. Microbiol. 40:216-226; US Patent application US20040253517), DNA dot blot hybridization (Borchardt et al., 2004. J. Clin. Microbiol. 42:146-150), and PCR-based restriction fragment length polymorphism (RFLP) analyses (Sellin et al., 2000. J. Clin. Microbiol. 38:3420-3428), utilize genetic polymorphisms in the capsular polysaccharide synthesis (cps) gene cluster to classify GBS strains into the corresponding serotypes. Genotypic methods complement phenotypic approaches and avoid problems of unreliable capsule expression, NT phenotypes, and new antigenic variants. Experiments conducted during the course of development of the present invention demonstrated a new PCR-based method that utilizes RFLP of the cps cluster to detect DNA polymorphisms in the cps cluster.

The cps cluster comprises genes cpsA-O, cpsR, cpsS, and cpsY (6, 8, 28), most of which are conserved across serotypes (Cieslewicz et al., supra). cpsG-K, however, are highly variable in serotypes Ia, Ib, and II to VII, whereas cpsE to -K are variable in serotype VIII (see FIG. 2a in Cieslewicz et al. supra). In addition, not all serotypes contain all cps genes.

I. Diagnostic Methods

As described above, the present invention provides methods for the molecular subtyping of Group B streptococci (GBS). In some embodiments, the method utilizes PCR based genotyping. For Example, in some embodiments, the present invention provides a PCR and restriction fragment polymorphism (RFLP) method that utilizes a single primer set. The methods of the present invention are able to identify multiple subtypes of GBS with a single primer set.

The methods of the present invention are suitable for use with GBS samples isolated from a variety of sources. Methods are known in the art for isolating GBS from blood samples. In other embodiments, GBS samples are isolated from rectal or vaginal swabs. In still further embodiments, GBS samples are isolated from sputum, bronchial swabs, spinal fluid or other bodily fluids. In yet other embodiments, purified recombinant or lab grown GBS samples are utilized.

In some embodiments (See e.g., Example 1), PCR primers are designed that flank the variable region of GBS capsular region. In preferred embodiments, a single set of primers that hybridize to homologous sites in all of the GBS serotypes sought to be serotyped is utilized to amplify the GBS nucleic acids present in the sample. The resulting fragments are subjected to restriction fragment length analysis. Restriction fragments are then compared to known restriction fragments for GBS serotypes in order to determine the serotype of the GBS present in the sample. Experiments conducted during the course of development of the present invention resulted in the identification of serotypes of GBS.

The method of the present invention are also suitable for the identification or serotype variants (e.g., comprising polymorphisms or mutations). For example, a GBS sample may be identified as a particular serotype and further identified as being a variant or mutant form of the serotype.

In some embodiments, the analysis is automated. Automated robotic systems are known in the art for the purification of samples and for set up of PCR and RFLP assays. In some embodiments, the analysis of assay data is further automated. In some embodiments, the level of automation and the choice of automation system is tailored to the size and volume of the analysis facility. For example, a small volume laboratory (e.g., in a primary care physician's office) may utilize a manual system or a partially automated system. Conversely, a large reference laboratory or high throughput drug screening facility may utilize a completely automated high volume system.

A. Diagnostic and Clinical Applications

The methods of the present invention find use in the diagnosis and screening of GBS infections. The methods of the present invention are able to distinguish more virulent (e.g., serotypes Ia, II, III, and IV) from less virulent serotypes. The serotype information finds use in the choice of treatment options. For example, individuals found to carry a more virulent strain may be given more aggressive treatment.

In some embodiments, a computer-based analysis program is used to translate the raw data generated by the detection assay (e.g., the serotype or serotype variant of GBS) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a bodily fluid or swab) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample or vaginal swab) and directly send it to a profiling center. Once received by the profiling service, the sample is processed and a profile is produced (i.e., serotype data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of transmission or severe GBS infection to a newborn) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

B. Research Applications

The method of the present invention further find use in research applications. For example, in some embodiments, the methods of the present invention find use in drug screening applications (See e.g., Section III below). In some embodiments, customized therapeutics are designed to a particular serotype or group of serotypes. In other embodiments, existing antibiotics are screened to determine the optimal drug for a particular serotype. Thus, the patient can be given an antibiotic that is more likely to be effective, thus decreasing the chance of the patient requiring a second course of a different antibiotic.

The method of the present invention further find use in basic research applications. For example, in some embodiments, the crystal structures of different variants are determined and used to perform structure function studies. The results of such structure function studies find use in identifying candidate drugs.

In yet other embodiments, the methods of the present invention find use in vaccine development. For example, in some embodiments, epidemiological studies are performed to determine the prevalent strains in a given population or geographical area. A vaccine is then generated to the most prevalent strains. In some embodiments, continual monitoring is utilized to track changes in prevalent strains. New vaccines are then developed at particular time intervals (e.g., every 1, 2, 5 or more years) that most closely match the prevalent strains. In other embodiments, vaccines are customized to a geographical region, socioeconomic group or ethnic group.

II. Kits

In some embodiments, the present invention provides kits for the detection of GBS serotypes. In some embodiments, the kits contain reagents specific for the isolation, amplification and restriction digest of GBS nucleic acid (e.g., sample collection materials, isolation reagents, oligonucleotide primers and restriction enzymes). In preferred embodiments, the kits contain all of the components necessary to perform a detection assay, including all controls, directions for performing assays, and any necessary software for analysis and presentation of results. In some embodiments, individual primers and reagents for detection of GBS serotypes are provided as analyte specific reagents. In other embodiments, the kits are provided as in vitro diagnostics. In yet other embodiments, the kits are provided as research reagents.

III. Drug Screening

In some embodiments, the present invention provides drug screening assays (e.g., to screen for antibiotics effective against GBS). In some embodiments, the screening methods of the present invention utilize specific serotypes of GBS. For example, in some embodiments, the present invention provides methods of screening for compounds that have specific antibiotic activity against a particular serotype of GBS (e.g., a particularly virulent subtype). In some embodiments, test compounds are evaluated for their ability to kill or decrease the growth of GBS.

In some embodiments, drug screening assays are performed in vitro. GBS (e.g., of a particular serotype) is cultured using an appropriate method. The GBS is then contacted with a test compound and the ability of the test compound to kill or inhibit the growth of the GBS is assayed. In some embodiments, the activity of the test compound is compared to antibiotics currently used in the treatment of GBS.

In other embodiments, drug screening assays are conducted in test animal (e.g., non-human animals) infected with GBS. Animals are first infected with a specific serotype of GBS. Test compounds are administered and the ability of the test compound to eliminate or decrease infection by GBS is assayed. In some embodiments, the activity of the test compound is compared to antibiotics currently used in the treatment of GBS.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med.

Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In other embodiments, test compounds and/or control compounds are known antibiotics or candidate antibiotics.

EXPERIMENTAL

The following example is provided in order to demonstrate and further illustrate certain preferred embodiments and aspects of the present invention and are not to be construed as limiting the scope thereof.

Example 1

Serotyping of GBS

A set of PCR primers (cpsG-F97, 5'-GTGTTCAT-TCAAACGGGTTACTCA-3' (SEQ ID NO:1); cpsL-R200, 5'-GAACTTAAAGAACCGCTCGTCTG-3'(SEQ ID NO:2)) in the conserved cpsG and cpsL flanking the variable region of the cps cluster that yield amplicons ranging in size from 4,577 bp (serotype IV cps cluster) to 6,248 bp (serotype V cluster) (Table 1). For serotype VIII, another forward primer targeting cpsR (cpsR8-F40, 5'-CCGGCAAGATATGGTG-GAT-3' (SEQ ID NO:3)) was utilized, which when used with the cpsL-R200 primer, produces a 4,551-bp PCR product (Table 1).

Figure 1:
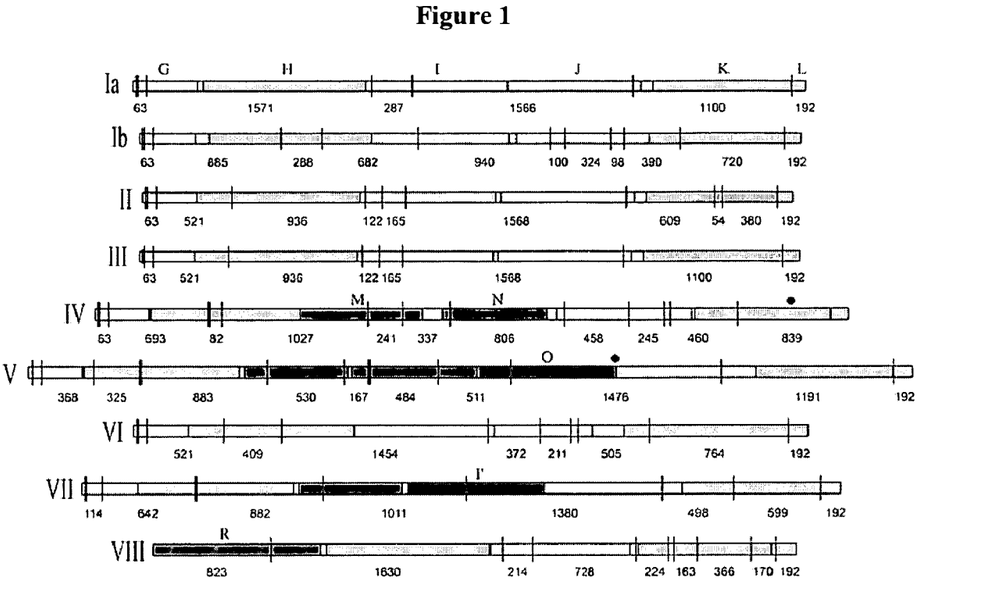
FIG. 1 shows a diagram representing the serotype-specific variable region within the group B streptococcal capsular polysaccharide synthesis gene (cps) cluster that is amplified by PCR.

Because of the sequence variability across serotypes within the region amplified, in silico digestion of the cps amplicons yields extensive RFLP among serotypes (FIG. 1). Based on the published cps sequences of nine GBS strains, digestion with DdeI of the predicted cps amplicons should generate 8 to 15 restriction fragments (Table 1).

141 GBS strains representing nine serotypes and NT strains as determined previously by the Lancefield method (Lancefield, 1934. J. Exp. Med. 59:441-458) at the National Center for *Streptococcus* (Edmonton, Alberta, Canada) were analyzed. A total of 45 strains, collected in Alberta between 1998 and 2000, were isolated from patients with invasive GBS disease (Davies et al., 2001. Pediatr. Infect. Dis. J. 20:879-884), and 36 strains were from colonized pregnant women (Davies et al., 2001. J. Infect. Dis. 184:285-291). An additional 60 strains were obtained from the American Type Culture Collection (NEM316), the University of Michigan (n=26) (5, 20, 21), Czech National Collection of Type Cultures (n=2), Norrlands Universitetssjuk-Ius (n=20) (Sellin et al., J. Clin. Microbiol. 38:3420-3428), and Channing Laboratory (n=11) (Tettelin et al., 2002. Proc. Natl. Acad. Sci. USA 99:12391-12396). Approval to obtain isolates from some pregnant women and newborns in the present study was granted by the Conjoint Medical Ethics Board of the University of Calgary. Informed consent was obtained from all study participants.

DNA was isolated by growing strains overnight in Todd-Hewitt broth incubated at 37° C. in $CO_2$ (Mo Bio Laboratories, Inc., Solana Beach, Calif.). The three primers (10 µM each) were pooled, and DNA fragments were amplified via PCR using 1.5 U of LA Taq (Takara Bio, Inc., Kyoto, Japan). The thermal cycle, initiated by a 1-min soak at 94° C., was run for 30 cycles (94° C. for 30 s, 58° C. for 30 s, and 68° C. for 6 min), followed by a 10-min soak at 72° C. The amplicons were digested with DdeI (New England Biolabs, Inc., Beverly, Mass.) overnight at 37° C., followed by electrophoresis on a 1.5% agarose gel and ethidium bromide staining.

The cps region was amplified in 139 (98.5%) strains representing nine serotypes, and DdeI digestions revealed 12 distinct restriction fragment patterns. With the exception of serotype II strains, the observed fragment sizes estimated using PRO-SCORE (DNA ProScan. 1999. PRO-SCORE, 3.36 ed. DNA ProScan, Inc., Nashville, Term) matched the predicted sizes. RFLP of the cps region was concordant with the serotype in 136 (96.4%) of 141 strains (Table 2); therefore, the distinct restriction patterns were designed with numbers and letters corresponding to the serotype (e.g., cps1a for serotype Ia).

Two strains originally designated as serotype III matched the cps1a and cps5 genotypes. Blinded re-serotyping using hyperimmune rabbit antisera to the GBS polysaccharide types (Manning et al., 2002. Epidemiology 13:533-539) was performed. Re-serotyping confirmed the cps5 genotype in one strain, suggesting an error in the original serotype. The cps1a strain was re-serotyped as NT, a result that may be a consequence of overexpression of the cpsH alleles (Chaffin et al., 2000. J. Bacteriol. 182:4466-4477).

All 13 serotype II strains produced the identical cps2 pattern, which differed substantially from the predicted DdeI digestion of the serotype II cps sequence in GenBank (AY375362 [8]). The present invention is not limited to a particular mechanism. Indeed, an understanding of the mechanism is not necessary to practice the present invention. Nonetheless, it is contemplated that the GenBank strain does not represent the primary serotype II GBS clone in circulation.

Among the 21 NT strains examined, 19 could be assigned a cps genotype after PCR amplification and DdeI digestion (Table 2). In two strains, however, no amplicons of the cps region were produced. Further evaluation of these strains with additional primer sets, including primers in cpsE and neuB (FIG. 1) paired with the reversed cpsG and cpsL primers and previously described (Sellin et al., supra) cps primers (lorfxfo and loEFrev), yielded no specific PCR products. These observations, along with reports of rare GBS strains that cannot be typed by other methods (Borchardt et al., 2004. J. Clin. Microbiol. 42:146-150; Sellin et al., supra), suggest that there are clones in the GBS population that have diverged in the conserved regions of cps locus.

Figure 2:
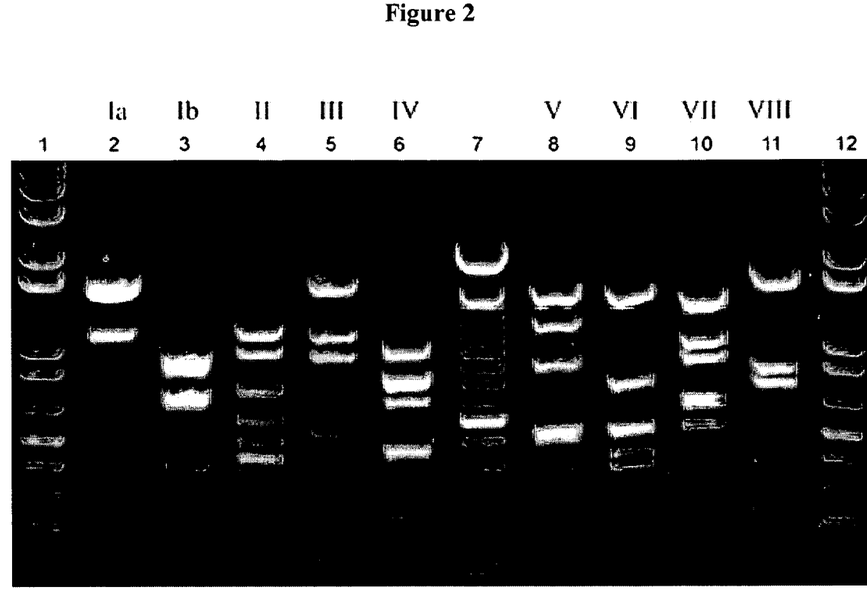
FIG. 2 shows PCR-based RFLP capsular typing method illustrating the observed banding patterns specific for each of the nine group B streptococcal serotypes. Lanes 2 to 6, serotypes Ia, Ib, and II to IV, respectively; lanes 8 to 12, serotypes V to VIII; lanes 1 and 12, 1-kb plus ladder; lane 7, 100-bp ladder.
Figure 3:
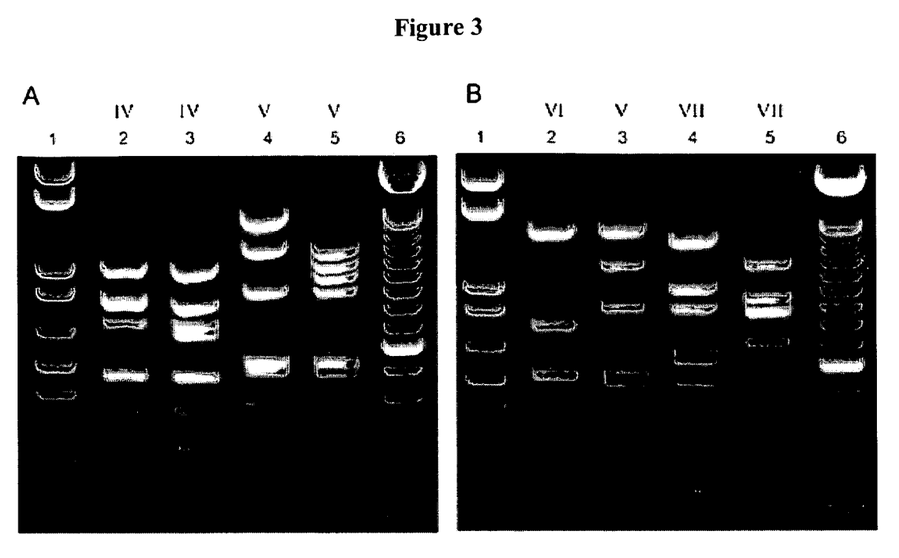
FIG. 3 shows restriction fragment banding patterns of cps allelic variants. (A) Lane 2, cps4.1; lane 3, cps4.2; lane 4, cps5.1; lane 5, cps5.2. (B) Lane 2, cps6; lane 3, cps5.1; lane 4, cps7.1; lane 5, cps7.2.

One advantage of the RFLP-based method is its ability to identify cps genotypic variants. Cps variants were recovered for serotypes IV, V, and VII but not for serotype III as described previously (Sellin et al., supra) (FIG. 2). For serotypes IV and V, the observed restriction patterns were similar to the predicted patterns (FIG. 3). The cps4.2 (serotype IV, allele 2) variant can be explained by an additional restriction site in the 839-bp fragment of cpsK (FIG. 1), whereas cps5.2 (serotype V, allele 2) appears to have an approximately 700-bp DNA insertion with additional restriction sites between cpsO and cpsJ (FIG. 1). The serotype VII variant pattern (cps7.2), originally identified by Sellin et al. (supra), differs substantially from the predicted pattern (FIG. 3).

In conclusion, the amplification and RFLP analysis of the cps gene cluster accurately reveals the genetic variation underlying the capsular variation of GBS strains. Genotyping the cps locus as described is inexpensive, is easy to perform, and can be used to classify NT isolates and identify cps allelic variants. In addition, it can identify novel, emergent, capsular types based on restriction pattern differences.

TABLE 1

Expected DNA fragment sizes of a 4,551-to 6,248-bp region of the group B streptococcal cps gene cluster after PCR and digestion with Dde1

| Capsule serotype | GenBank accession no. | Reference(s) | Predicted cps amplicon length (bp) | Expected no. of cut sites | Expected restriction fragment lengths (bp)$_a$ |
|---|---|---|---|---|---|
| Ia | AB028896 | 28 | 4,814 | 7 | 14, 21, 63, 192, 287, 1,100, 1,566, 1,571 |
| Ib | AB050723 | 27 | 4,717 | 12 | 14, 21, 63, 98, 100, 192, 288, 324, 390, 682, 720, 885, 940 |
| II | AY375362 | 8 | 4,645 | 11 | 14, 21, 54, 63, 122, 165, 192, 380, 521, 609, 936, 1,568 |
| III | AF163833, NC_004368 | 14, 23 | 4,702 | 9 | 14, 21, 63, 122, 165, 192, 521, 936, 1,100, 1,568 |
| IV | AF355776 | 7 | 5,304 | 14 | 11, 14, 21, 43, 63, 82, 241, 245, 337, 458, 460, 693, 806, 839, 1,027 |
| V | AF349539, NC_004116 | 7, 26 | 6,248 | 14 | 11, 12, 14, 21, 63, 167, 192, 325, 368, 484, 511, 530, 883, 1,191, 1,476 |
| VI | AF337958 | 7 | 4,577 | 11 | 14, 21, 51, 63, 192, 211, 372, 409, 505, 521, 764, 1,454 |
| VII | AY376403 | 8 | 5,364 | 10 | 11, 14, 21, 114, 192, 498, 599, 642, 882, 1,011, 1,380 |
| VIII | AY375363 | 8 | 4,551 | 9 | 41, 163, 170, 192, 214, 224, 366, 728, 823, 1,630 |

$_a$Dde1 restriction fragments of cps PCR product. Underlining denotes fragments that can be resolved on a 1.5% agarose gel.

TABLE 2

Capsule genotypes based on RFLP of the cps gene cluster

| Capsule | No of strains | Capsule genotype (no. of strains$_a$) |
|---|---|---|
| Ia | 8 | cps 1a (8) |
| Ib | 7 | cps 1b (7) |
| II | 13 | cps2 (13) |
| III | 38 | cps3 (36), cps1a (1), cps5.1 (1) |
| IV | 16 | cps4.1 (9), cps4.2 (6), cps6 (1) |
| V | 11 | cps5.1 (10), cps6 (1) |
| VI | 9 | cps6 (8) cps5.1 (1) |
| VII | 8 | cps7.1 (6), cps7.2 (2) |
| VIII | 10 21$_b$ | cps8 (10) cps1a (2), cps1b (4), cps5.1 (9), |
| NT | | cps5.2 (2), cps6 (1), cps8 (1) |

$_a$A complete strain list with capsule genotypes is provided in the supplemental material.
$_b$The capsular genotype could not be determined for two NT strains.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method, comprising:
   a) providing a sample comprising group B *streptococcus*;
   b) contacting said sample with at least two primers under conditions such that an amplicon comprising at least a portion of at least one capsular gene of said group B *streptococcus* is produced, wherein said first primer consists of SEQ ID NO:3 and the second primer hybridizes to the cpsL gene;
   c) contacting said amplicon with at least one restriction enzyme under conditions such that a plurality of restriction fragments are generated; and
   d) determining the serotype of said group B *streptococcus* based on the size of said plurality of restriction fragments.

2. A kit, comprising:
   a) at least two primers that amplify at least a portion of at least one capsular gene of a group B *streptococcus* nucleic acid, wherein said first primer consists of SEQ ID NO:3 and the second primer hybridizes to the cpsL gene; and
   b) a restriction enzyme that recognizes at least one restriction site in said at least one capsular gene of said group B *streptococcus*.

3. The kit of claim 2, wherein said restriction enzyme is DdeI.

* * * * *